United States Patent
Brinegar et al.

(10) Patent No.: US 6,639,067 B1
(45) Date of Patent: Oct. 28, 2003

(54) CONTINUOUS PROCESS FOR THE PRODUCTION OF ANHYDROSUGAR ALCOHOLS

(76) Inventors: Willard C. Brinegar, 62 Molly's Point Rd., Southport, ME (US) 04576; Michael Wohlers, An Der Grungesweide 1, Eschborn (DE), D-65760; Michael A. Hubbard, 8 Surrey La., Pittsford, NY (US) 14534; Edward G. Zey, 522 Evergreen Dr., Corpus Christi, TX (US) 78412; George Kvakovszky, 3068 Meadow Lake Dr., Slidell, LA (US) 70461; Thomas H. Shockley, 4606 Champions Dr., Corpus Christi, TX (US) 78413; Rainer Roesky, 10, Rue des Cerisiers, Saint Quentin Fallavier Cedex 16 (FR), F-38070; Uwe Dingerdissen, Linneweg 1, Seeheim-Jugenheim (DE), D-64342; Werner Kind, Zum bach 5, Kelkheim (DE), D-65779

( * ) Notice: Subject to any disclaimer, the term of this patent is extended or adjusted under 35 U.S.C. 154(b) by 0 days.

(21) Appl. No.: 09/786,716

(22) PCT Filed: Jan. 11, 1999

(86) PCT No.: PCT/US99/00537

§ 371 (c)(1), (2), (4) Date: Sep. 27, 2001

(87) PCT Pub. No.: WO00/14081

PCT Pub. Date: Mar. 16, 2000

(30) Foreign Application Priority Data

Sep. 9, 1998 (DE) .......................... 198 41 032

(51) Int. Cl.[7] .......................... C07G 17/00; C07H 1/00; C07H 3/00; C08B 37/00; C13K 5/00

(52) U.S. Cl. .................... 536/126; 536/124; 536/123.1; 536/55.3; 536/18.5; 536/18.6; 536/18.7

(58) Field of Search ............................... 536/4.1, 17.2, 536/18.5, 18.6, 18.7, 55.3, 123.1, 123.13, 124, 126, 127; 428/35.7, 36.1, 36.3, 36.8, 36.92

(56) References Cited

U.S. PATENT DOCUMENTS

| 3,454,603 | A | * | 7/1969 | Hartmann | 260/347.8 |
|---|---|---|---|---|---|
| 4,297,290 | A | * | 10/1981 | Stockburger | 260/410.6 |
| 4,506,086 | A | * | 3/1985 | Salzburg et al. | 549/464 |
| 4,739,043 | A | * | 4/1988 | Defaye et al. | 536/18.6 |
| 5,395,455 | A | * | 3/1995 | Scott et al. | 127/37 |
| 6,063,495 | A | * | 5/2000 | Charbonneau et al. | 428/364 |
| 6,126,992 | A | * | 10/2000 | Khanarian et al. | 427/162 |
| 6,140,422 | A | * | 10/2000 | Khanarian et al. | 525/176 |

OTHER PUBLICATIONS

Hicks et al. Can. J. Chem. (1974), 3367–3372.*
Montgomery et al. J. Chem. Soc. 1947, 433–436.*
Defaye et al. Carbohydrate Research (1990), 205, 191–202.*
Fletcher et al. J. Am. Chem. Soc. (1946), 68, 939–941.*

* cited by examiner

*Primary Examiner*—James O. Wilson
*Assistant Examiner*—Patrick Lewis

(57) ABSTRACT

A process is described for continuous production of anhydrosugar alcohol by continuous introducing of sugar alcohols and/or monoanhydrosugar alcohols into a reaction vessel and dehydration in the presence of an acid catalyst and solvent in which the resultant reaction product is soluble. Water and the solvent having the dissolved reaction product are each cointinuously removed from the reaction vessel. The reaction product is separated from the removed solvent and the product is optionally purified to a purity of 99.0% the solvent is recycled in the reaction vessel.

28 Claims, 3 Drawing Sheets

CONTINUOUS PROCESS FOR THE PRODUCTION OF ANHYDROSUGAR ALCOHOLS

This application claims priority from DE 198 41 032.8, filed on Sep. 9, 1998.

A process for producing anhydrosugar alcohols, both monoanhydrosugar alcohols and dianhydrosugar alcohols, by dehydration of the associated sugar alcohols or monoanhydrosugar alcohols using a catalyst and an organic solvent is described, wherein the organic solvent is recycled during the process, and wherein the resulting anhydrosugar alcohols are very pure.

RELATED APPLICATIONS

This application claims priority from German utility application 198 34 778, filed Sep. 9, 1998. Further, the following application Ser. No. PCT/US99/00539, filed on even date herewith, contains related subject matter: PROCESS AND PRODUCTS OF PURIFICATION OF ANHYDROSUGAR ALCOHOLS. The subject matter of each of the above-mentioned applications is hereby incorporated by reference.

BACKGROUND OF THE DISCLOSURE

Anhydrosugar alcohols, whether they are monoanhydrosugar alcohols or dianhydrosugar alcohols, are known to be produced with the aid of various acid catalysts by dehydration of the associated sugar alcohols or monoanhydrosugar alcohols. Examples of these catalysts include sulfonated polystyrenes ($H^+$ form) (German Patent DE 3 041 673 C2; Canadian Patent Disclosure CA 1 178 288 A1); and various mineral acids, such as HCl (U.S. Pat. No. 4,169,152; German Patent Disclosure DE 3 233 086 A1), $H_3PO_4$ (East German Patent Disclosure DD 1 32 266; Can. J. Chem., 52 (19) 3362–72 (1974)), HF (International Patent Disclosure WO 89/00162 A; Carbohydr. Res. 205 (1990) 191–202) and $H_2SO_4$ (German Patent Disclosures DE 3 521 809 A1 and DE 3 229 412 A1).

These processes are often performed in the presence of a solvent. As solvents, water (CA 1 178 288 A1; European Patent Disclosure EP 0 052 295 B1) and organic solvents such as toluene or xylene (Przem. Chem. 48 (11) 665–8 (1969)) are known.

Batch processes for the preparation of dianhydrosugar alcohols by acid hydrolysis have been described in numerous patents and articles, for example, U.S. Pat. Nos. 3,454,603; 4,564,692; and 4,506,086; Canadian Patent 1178288; and articles J. Am. Chem. Soc., 68(5) pp. 939–941 (1946); J. Chem. Soc., p. 433–436 (1947); Przem. Chem. 48(11) pp. 665–668 (1969); and Pr. Nauk. Inst. Technol. Org. Tworzyw Sztucznych Politech. Wroclaw. No 3., p. 3–14 (1971).

In particular, a batch process for the formation of the dianhydrosugar alcohol isosorbide has been described in the literature as a two step process involving intramolecular dehydration of sorbitol to sorbitan (1,4-monoanhydrosorbitol), and further reaction of sorbitan to isosorbide (1,4:3,6-dianhydrosorbitol) in an acid catalyzed reaction, or dehydration, and cyclization. In this process, an aqueous solution of sorbitol is charged to a batch reactor. The temperature is increased to 130–135° C. under vacuum (35 mm Hg) to remove the water. When the sorbitol melt is free of water, a catalyst, usually sulfuric acid, is added and the temperature and vacuum levels are maintained. The operable temperature range of the reaction is very narrow. Higher temperatures lead to decomposition and charring of the end product, while lower temperatures inhibit the reaction rate due to difficulties in removal of the water of reaction. This reaction produces isosorbide and a higher molecular weight byproduct. The byproduct is presumably produced by water elimination between two or more sorbitol molecules, but its exact nature is not clearly defined. See starch/stärke (1986), 38(c), 26–30 and Roland Beck, Pharm. Mfg Inc. (1996), 97–100.

As described above, the known processes for the production of anhydrosugar alcohols are discontinuous batch processes producing a high molecular weight byproduct. There is no known teaching of performing the process continuously, or of recycling the solvent for use during the process. However, a continuous process for the production of anhydrosugar alcohols is desirable to facilitate large scale, economical production of both mono- and dianhydrosugar alcohols.

There is also an absence of teachings in the art regarding purification of the produced anhydrosugar alcohol in order to achieve a level of purity acceptable for use in such end products as polymers. Polymers require a high degree of purity in the starting materials in order to achieve clarity in the end product. Impurities in the starting materials manifest as discolorations in the polymeric product, usually of a yellow to brown color. This coloration interferes with the use of the polymer for production of certain articles of manufacture, such as optical disks, fibers, films, sheets and containers, all of which require a high degree of clarity.

Crude anhydrosugar alcohols contain contaminants. For example, crude isosorbide contains the degradation products of sorbitol, sorbitan and isosorbide, which cause the crude isosorbide to have a light yellow to brownish color. Therefore, additional process steps for purifying the product are necessary before use.

Commercially available anhydrosugar alcohols are also of unacceptable purity for the production of polymers. For example, commercially available isosorbide, though purified and appearing white in its crystalline form, turns yellow or brown upon annealing to temperatures $\geq 250°$ C., which is lower than the temperature required for the formation of polymers, indicating that a resultant polymer would likely be discolored. Thus, a means of making a purer product than what is commercially available or available through known manufacturing processes is desired.

Processes known for use in purification of anhydrosugar alcohols include distillation, which can occur with or without the addition of boron compounds, for example in the form of boric acid (U.S. Pat. No. 3,160,641) or sodium borohydride, use of an anion exchange resin (U.S. Pat. No. 3,160,641), and recrystallization from organic solvents such as methyl ethyl ketone or ethyl acetate (U.S. Pat. No. 3,454,603).

SUMMARY OF THE DISCLOSURE

The present disclosure relates to a process for producing very pure anhydrosugar alcohols which is economical and produces good yields, in which the formation of byproducts and contaminants is minimized, and which can be performed on a large industrial scale continuously without interruption for a relatively long time.

A preferred embodiment provides for a process of producing anhydrosugar alcohols wherein the process includes the steps of introducing at least one sugar alcohol or monoanhydrosugar alcohol into a reaction vessel; dehydrating the sugar alcohol or monoanhydrosugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel.

Another preferred embodiment further includes purifying the separated reaction product by distillation, recrystallization, or a combination thereof.

Yet another preferred embodiment provides for a process of producing anhydrosugar alcohols wherein the process includes the steps of introducing at least one sugar alcohol or monoanhydrosugar alcohol into a reaction vessel; dehydrating the sugar alcohol or monoanhydrosugar alcohol in the presence of an acid catalyst and a solvent to form a reaction product which is at least partly soluble in the solvent; removing water from the reaction vessel; removing solvent comprising the dissolved reaction product from the reaction vessel; separating the reaction product from the removed solvent; and recycling the solvent into the reaction vessel, wherein the steps of introducing in the starting materials, removing water, removing solvent and recycling the solvent occur simultaneously.

In preferred embodiments, it is desirable that the solvent be an organic solvent, the acid catalyst be a soluble acid or an acid anion exchange resin, and the reaction product be separated from the solvent by means of extraction. However, other materials and methods are contemplated for use, as disclosed herein.

BRIEF DESCRIPTION OF THE DRAWINGS

Preferred embodiments of the invention are set forth in attached FIGS. 1–3 as follows.

DETAILED DESCRIPTION OF PREFERRED EMBODIMENTS

Figure 1:
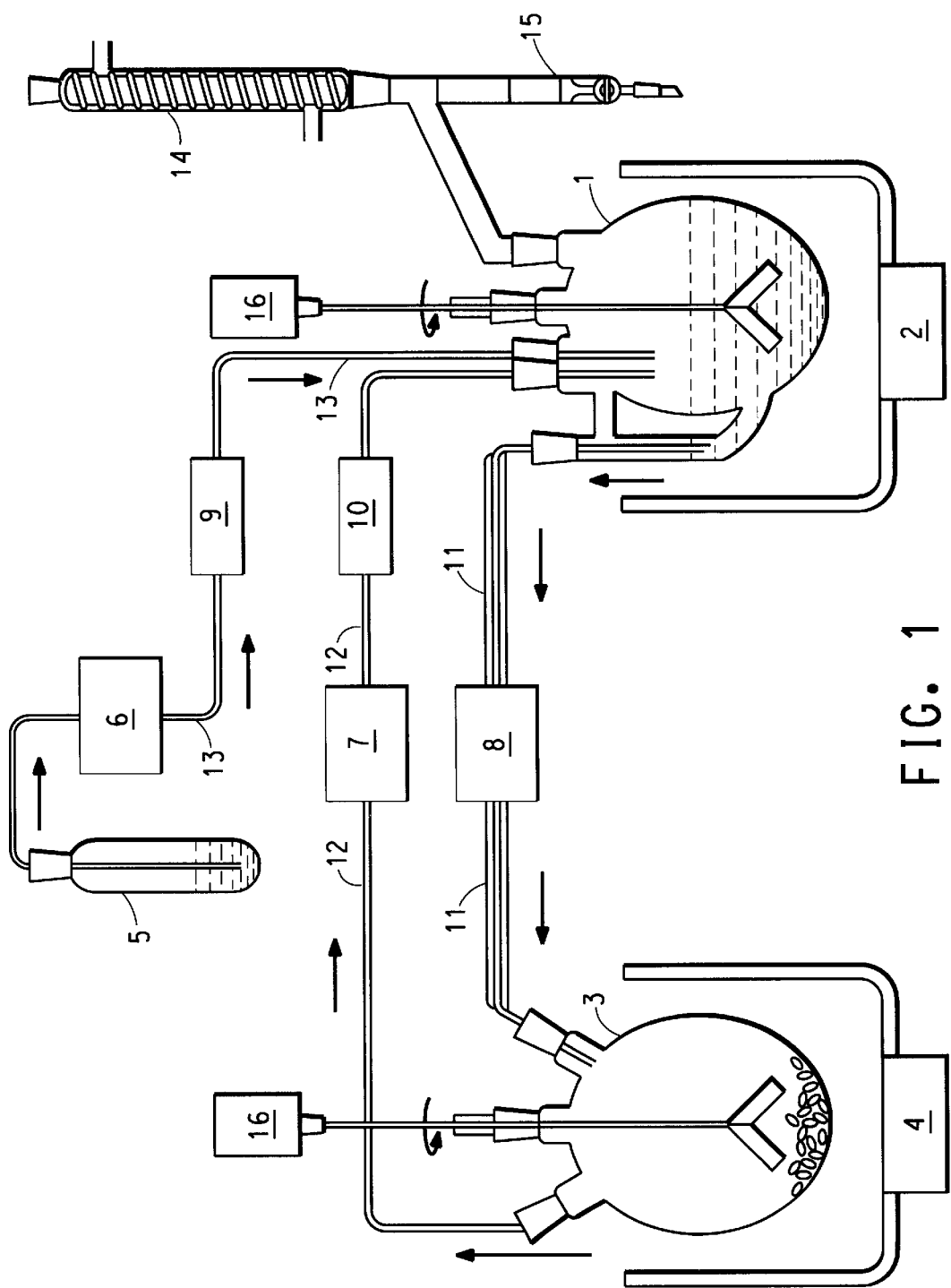
FIG. 1 illustrates a preferred embodiment of the continuous process of the invention.

The present disclosure describes a process for the production of mono- and dianhydrosugar alcohols, preferably of extremely high purity.

The process is directed toward the production of anhydrosugar alcohols and generally includes the steps of introducing at least one sugar alcohol or monoanhydrosugar alcohol into a reaction vessel; dehydrating the sugar alcohol or monoanhydrosugar alcohol in the presence of an acid catalyst and a solvent to form a reaction product which is at least partly soluble in the solvent; removing water from the reaction vessel; removing solvent comprising the dissolved reaction product from the reaction vessel; separating the reaction product from the removed solvent; and recycling the solvent into the reaction vessel. Optionally, the process may further include an additional purification step. Further, the process may be continuous such that the steps of introducing in the starting materials, removing water, removing solvent comprising the dissolved reaction product and recycling the solvent after separation from the reaction product occur simultaneously.

Typical sugar alcohols, in particular pentites and hexites, are suitable for use in the process as starting materials. The starting materials may be sugar alcohols, monoanhydrosugar alcohols, or a mixture thereof. In particular, preferred starting materials include arabinitol, ribitol, D-glucitol (also known as D-sorbitol or sorbitol), D-mannitol (mannitol), galactitol and iditol. The use of sorbitol is particularly desirable because sorbitol is readily available and can be obtained on a large industrial scale by the reduction of glucose with hydrogen, as known to one of ordinary skill in the art.

The catalysts used to facilitate the dehydration reaction are acid catalysts. Several types of acid catalysts may be used, each having specific advantages and disadvantages. One class of acid catalyst that may be used includes soluble acids. Examples of such acid catalysts include sulfuric acid, phosphoric acid, p-toluene sulfonic acid, methanesulfonic acid and the like. Sulfuric acid is a preferred catalyst from this class. Alternatively, acid anion exchange resins may also be used, such as sulfonated polystyrenes. A preferred acid anion exchange resin is AG50W-X12 from BioRad. Inorganic ion exchange materials may also be used, such as acidic zeolites. In particular, H-beta zeolite from Degussa may be used in the process disclosed herein.

All of the above described types of acid catalyst may be used in the process described herein. Each has specific advantages. For example, soluble acids such as sulfuric acid provide long term catalytic stability during the reaction, permitting the process to continue for long periods of time without recharging the catalyst. However, these catalysts also tend to promote the formation of an unwanted byproduct, a dark colored oligomeric residue which may be produced in amounts up to about 10%, and sometimes even greater. Alternatively, acid ion exchange resins produce little or no residue but do not at this time provide long term catalytic stability. Therefore, either type of acid catalyst may be selected with its specific limitations and advantages in mind, allowing the formation of a process with long term stability or minimal byproduct production. Alternatively, it may be possible to devise a system incorporating both types of catalysts or a different catalyst which produces long term stability while minimizing byproduct formation.

The solvent useful for the process described herein preferably forms an azeotropic mixture with water, or has a boiling point greater than that of water (100° C.). Desirably, the solvent has a boiling point of 120–150° C., preferably at least 130° C. Preferred solvents include organic solvents but exclude esters, such as ethyl acetate (EtOAc), because an ester may form undesirable transesterification products during the dehydration reaction. The solvents of the invention perform a dual function by facilitating the removal of water from the reaction mixture and acting as a solvent for the reaction product. The reaction product should be much more soluble in the solvent than the starting material, catalyst or any byproducts or intermediates of the reaction. Preferably, the solubility of the starting material, catalyst and any potential reaction intermediates or byproducts is as low as possible in the organic solvent of the process in order to assure a high degree of purity in the reaction product. Examples of suitable organic solvents include, but are not limited to, xylene, anisole, dichlorobenzene, nonane, n-octane, cumene, butyl ether and ethyl benzene. Preferably, the solvent of the process is selected from xylene, anisole, dichlorobenzene and nonane. More preferably, the solvent is selected from xylene and anisole, with xylene being the most preferred solvent.

It is possible to perform one or two dehydrations of the starting sugar alcohol during the reaction, producing a mono- or dianhydrosugar alcohol. The reaction further may be controlled so as to produce a combination of mono- and dianhydrosugar alcohols by adjusting either the reaction conditions or the starting materials, which may contain both sugar alcohols and monoanhydrosugar alcohols.

The dehydration is desirably performed at elevated temperatures between 80° C. and 180° C., preferably at temperatures between 120° C. and 140° C., and most preferably between 130° C. and 140° C. It is advantageous to perform the dehydration under a protective or non-reactive gas atmosphere, particularly nitrogen. The dehydration can be performed at atmospheric pressure, although elevated or reduced pressures can also be used with minor adjustments to process parameters such as time and temperature, as known to one of ordinary skill in the art.

During the dehydration, the reaction mixture is preferably kept under reflux conditions in order to remove water by azeotropic distillation. Water may also be removed by other methods known in the art, such as evaporation.

The dehydration reaction in the reaction vessel can be performed in various ways. For instance, it is possible to keep the quantity of supplied starting material, compared with the organic solvent present, so high that two or more phases form in the reaction vessel. These phases comprise at least a lower aqueous phase comprising molten sugar alcohol and/or anhydrosugar alcohol, and an organic phase above the aqueous phase in which the reaction product that has formed dissolves rapidly. The organic phase is removed from the reaction vessel along with the dissolved reaction product by pumping, decanting or other methods known in the art. Such two phase systems are demonstrated in the Examples herein, particularly Examples 2–6, which exemplify the use of various solvents, catalysts, dosages of starting materials and solvent recirculation rates. The organic solvents useful in the dehydration reaction may have a density lower than that of the aqueous phase, as described above, or higher than that of the aqueous phase. If organic solvents with higher densities than the aqueous phase are used, the aqueous phase forms the upper layer and the dissolved product is present in the lower organic layer.

It is possible to use a relatively large quantity of organic solvent into which the sugar alcohols or the monoanhydrosugar alcohols, catalyst and water are metered. In this case, it is unnecessary to allow the development of two phases in the reaction chamber. Instead, it is preferred that the solvent in which the reaction product is dissolved be drawn off continuously, causing the dehydration to be done in a steady state of equilibrium wherein the moles of starting materials metered in and the moles of dissolved reaction product removed are equivalent to one another. The continuous drawing off of the reaction product in the organic solvent from the reaction vessel drives the reaction forward and greatly increases yield and productivity.

In either case, the dehydration can be performed in such a way that the catalyst is added in the requisite quantity once, and further catalyst is added only when necessary. However, it is also possible to add the catalyst in dosed fashion continuously during the dehydration.

The high temperature of the dehydration reaction promotes rapid dehydration of the starting materials. However, it may also promote the formation of byproducts and/or the further conversion of the desired mono- or dianhydrosugar alcohols to undesired secondary products over time. Therefore, for both one phase and two phase reactions, it is desirable to divert the resultant reaction product from the reaction chamber rapidly to protect it against further decomposition. Preferably, the reaction product is drawn off from the reaction vessel continuously during the course of the dehydration reaction.

After dehydration of the starting material is completed, the acid catalyst may be deactivated and/or removed from the solvent containing the reaction product, which preferably has been removed from the reaction vessel. In the case of soluble acid catalysts, the deactivation may be accomplished by any method known in the art, such as addition of a metal hydroxide base to form an insoluble salt which will precipitate out of solution. In particular, calcium hydroxide may be used in the process disclosed herein. Polymeric or inorganic ion exchange materials may be recovered by filtration. Before reuse, reactivation may be necessary.

To separate the reaction product from the solvent, the reaction product may be recrystallized from the solvent. Alternatively, a liquid-to-liquid extraction can be performed instead of the recrystallization using water or lower aliphatic alcohols such as ethanol or methanol, and may be conducted as part of the continuous process.

For example, the solvent containing the reaction product may be removed from the reaction vessel and combined with water or a lower aliphatic alcohol, such as methanol or ethanol. The reaction product is extracted from the solvent into the water or aliphatic alcohol, which is then decanted or otherwise separated from the solvent. The reaction product can be recrystallized from the water or lower aliphatic alcohol, while the solvent is recycled for use in the reaction vessel. It is preferable that the solvent and the water or lower aliphatic alcohol form a two phase system in order to facilitate separation of the solvent for reuse in the process of the invention.

The extraction of the reaction product by the organic solvent from the reaction mixture under reaction conditions is a reactive extraction which removes the reaction product from the reaction mixture and which furthermore aids in purifying the reaction product. By the reactive extraction, the reaction product is separated from unreacted starting material, reaction intermediates and reaction byproducts. The organic solvent comprising the dissolved reaction product is drawn off from the reaction vessel. The dissolved reaction product is then separated from the drawn-off organic solvent by cystallization or by means of liquid-liquid extraction with water or lower aliphatic alcohols like methanol or ethanol. If separated by crystallization, the reaction product is obtained as a solid. If separated by liquid-liquid-extraction, the reaction product is obtained as a solution in water or lower aliphatic alcohols like methanol or ethanol. The reaction product obtained by the reactive extraction described above may be purified further if desired. However, the continuous process described herein comprises intrinsic purification steps resulting in a more pure reaction product than would otherwise result from batch processes as known heretofor in the art.

Further purification of the crude reaction product may occur by distillation, recrystallization, melt recrystallization or a combination thereof, as described in detail in copending application Ser. No. 09/857,574, filed on even date herewith. A combination of distillation and recrystallization from an aliphatic alcohol such as methanol or ethanol is preferred in order to minimize the number of purification steps while maximizing the purity of the reaction product. This purification of the reaction product may occur as part of the continuous process or in a separate process. In either case, the purity of the resultant anhydrosugar alcohol should be at least 99.0%, preferably at least 99.5%, most preferably at least 99.8%, and preferably meets the purity requirements for use in polymer production, as set forth at least in copending application Ser. No. 09/857,574, filed on even date herewith.

The most effective way to purify the reaction product is a combination of vacuum distillation and recrystallization from lower aliphatic alcohols, preferably methanol or ethanol. The addition of hydride ions, such as in the form of sodium borohydride, $NaBH_4$, or lithium aluminum hydride, to the distillation is not necessary if further purification of the reaction product is to be done before use of the reaction product. If distillation is the only form of purification used, then the addition of hydride ions, preferably borohydride ions, most preferably in the form of sodium borohydride, is preferred to achieve greater purity.

In a preferred embodiment, at least the steps of introducing the starting materials, removing water from the reaction, removing solvent and recycling the solvent to the reaction flask are performed simultaneously, creating a continuous process for the formation of anhydrosugar alcohols.

The process of the invention described herein has the surprising and unexpected result of furnishing an economical large scale method of manufacturing anhydrosugar alcohols. It is a further surprising result that the anhydrosugar alcohols made by the process of the invention are exceptionally pure.

A preferred process of the invention will now be described in relation to FIG. 1.

As shown in FIG. 1, the dehydration takes place in a vessel (1), which is provided with supply lines for the starting materials such as sugar alcohol or aqueous sugar alcohol solution, as well as the organic solvent and acid catalyst. In the present case, sugar alcohol or aqueous sugar alcohol solution and, if necessary, a catalyst is supplied from the supply vessel (5) via a pump (6) and a heater (9) to vessel (1) by a single line (13). Vessel (1) is heated by means of an oil bath (2) to temperatures of about 80–180° C., preferably 120–160° C., most preferably 130–140° C.

The reaction mixture thus formed in vessel (1) is mixed during the dehydration reaction by means of an agitator (16). A distillation head with a cooler (14) is used to distill off the water that results from, in part, the dehydration process. This water is condensed in the cooler and any organic solvent that may have been jointly distilled in the distillation is separated from it. The water and solvent form two different layers, which can easily be separated, such as in the water separator (15). The water can be drained off, and the solvent, which is preferably lighter than water, flows continuously back into the reaction chamber. A heatable drain line (11) is used for continuously drawing off solvent from the reaction chamber by means of a pump (8). This solvent, containing dissolved reaction product, is carried to a recrystallization vessel (3) which is at a lower temperature than the reaction chamber, preferably below 10° C. The low temperature is maintained by ice bath (4). There, the reaction product is recrystallized from the organic solvent. The recrystallization vessel may be provided with an agitator (17) and with other typical measurement instruments such as temperature sensors and the like. The crystals can be carried off continuously or discontinuously. The solvent can be drawn off continuously, optionally reprocessed, and returned to the dehydration mixture via line (12) and pump (7). It is advantageous to heat the solvent to a suitable temperature before returning it to the dehydration mixture, for example, by passing it through a heat exchanger (10).

Figure 2:
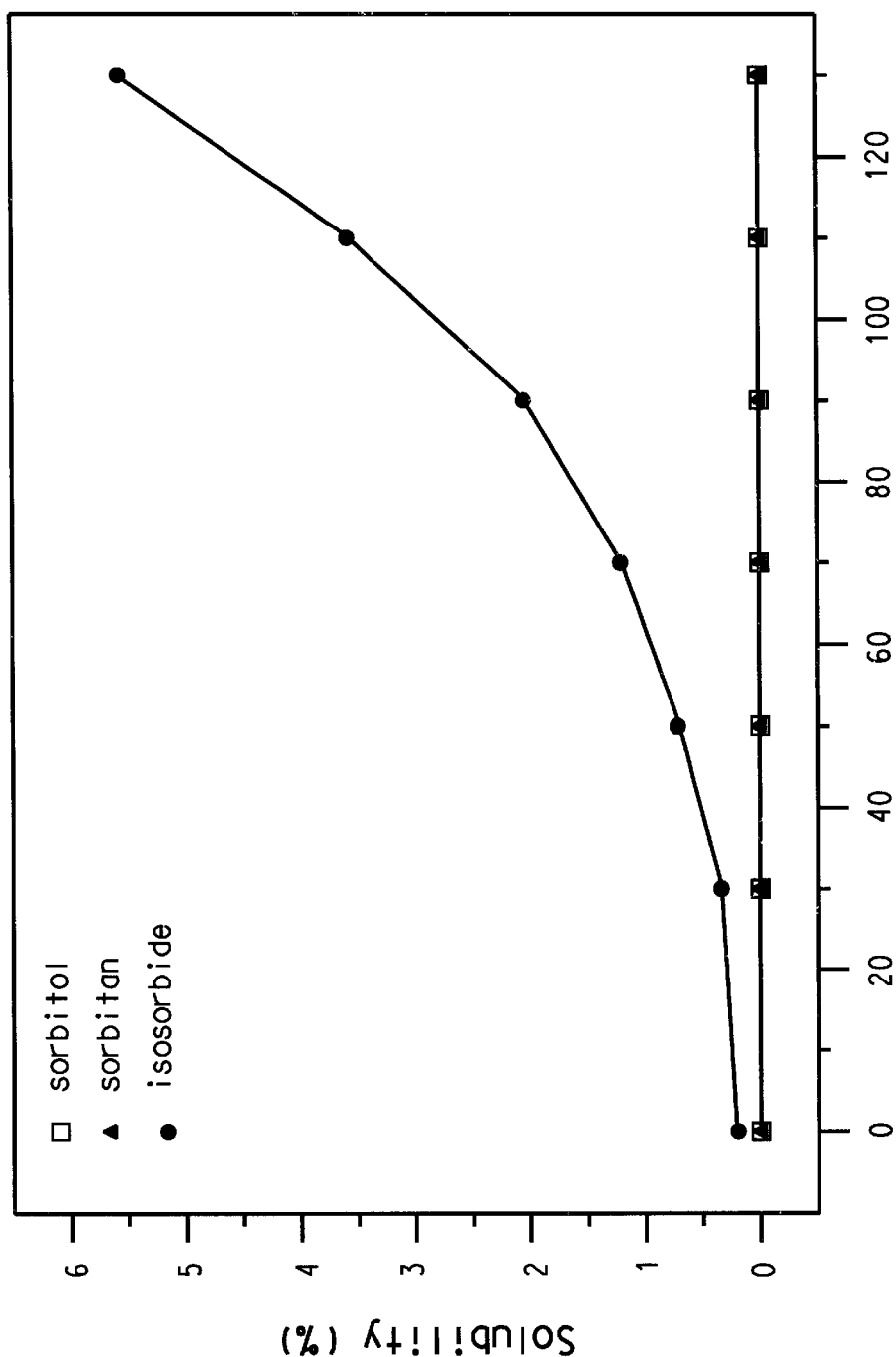
FIG. 2 illustrates the solubility of sorbitol, sorbitan and isosorbide in xylene.

The process is preferably performed under conditions in which the resultant reaction product has substantially better solubility in the solvent than the starting material or catalyst. It can be seen from FIG. 2 that the differences in solubility between sorbitol and the desired end product isosorbide are considerable at temperatures of 80° C. and higher.

The dehydration temperature of the process is optimally between 80° C. and 180° C., preferably between 120° and 160° C., and most preferably between 130° C. and 140° C. However, the temperature of dehydration may vary from these ranges as required by changes in starting material, reaction pressure or other process parameters, as known to one of ordinary skill in the art.

It is understood that a favorable temperature range for dehydration will be selected on the basis of a few preliminary experiments with suitable solvents and catalysts using the desired starting material, as known to one of ordinary skill in the art. The pressure of the reaction may be changed from atmospheric pressure if desired, with appropriate corresponding changes in the temperature of the reaction as known to those skilled in the art.

Because of the high purity of the product, the process of the invention is especially well suited for producing monomers used as starting materials for polymer production and purification as described in copending application, Ser. No. 09/857,574, filed of even date herewith. For example, isosorbide produced by this invention is of such high quality as to be used for making polymers, in particular polyesters, and products made therefrom, such as fibers, containers, sheets, films and optical disks, as described, for example, in copending U.S. patent applications Ser. No. 09/064,844 (which issued as U.S. Pat. No. 5,959,066); Ser. No. 09/064,950 (which issued as U.S. Pat. No. 6,063,465); Ser. No. 09/064, 846 (which issued as U.S. Pat. No. 6,126,992); Ser. No. 09/064,858 (which issued as U.S. Pat. No. 5,958,581); Ser. No. 09/064,826 (which issued as U.S. Pat. No. 6,140,422); Ser. No. 09/064,719 (which issued as U.S. Pat. No. 6,063, 495); Ser. No. 09/064,862 (which issued as U.S. Pat. No. 6,025,061); and Ser. No. 09/064,720 (which issued as U.S. Pat. No. 6,063,464), all filed Apr. 23, 1998, which are incorporated herein in their entirety by reference. In particular, polymers incorporating the anhydrosugar alcohols produced by the process described herein may be formed by polycondensation of the anhydrosugar alcohol with multi-functional containing materials such as polycarboxylic monomers, polycarboxylic acid halides such as acid chloride, polycarbonate monomers such as diphenylcarbonate or phosgene, isocyanates such as tolenene diusocyanate and methylene diphenylisocyanate and dicarboxylic acids, such as terephthaloyl moieties, or dimethyl esters thereof and, optionally, aliphatic diols, such as ethylene glycol.

All references cited herein are incorporated in their entirety by reference. The following examples will demonstrate the process of the invention. The scope of the invention is not determined by the examples, but is set forth in the above specification and the following claims, and includes all equivalent materials and methods as known to one of ordinary skill in the art.

In the examples below, dehydrations using sorbitol as the starting material are described.

EXAMPLE 1

In a continuous process of the invention, a reaction flask is loaded with xylene as solvent, water, and $H_2SO_4$ as catalyst. The stirring rate is adjusted to 150 rpm. The precipitation flask is loaded with xylene, and the stirring rate is adjusted to 300 rpm. Both flasks are purged with inert gas (nitrogen) to prevent oxidation of the sugar derivatives by air. An oil bath is heated to about 170° C., and a cooling bath is cooled to about −15° C. Pumps are started, and the pumping rates are adjusted to maintain the xylene amounts in the reaction flask and precipitation flask at a rate of at least 2 to 1, respectively. Heaters are switched on for heating materials entering the reaction flask. The temperature of the xylene/reaction product mixture is 85° C.–95° C., while the temperature of xylene returning to the reaction flask after separation from the reaction product is about 120° C. The inner temperature of the xylene/reaction product transport line has to be above the melting point of isosorbide to prevent precipitation of isosorbide and thus blocking of the line, and is below a temperature at which evaporation of the xylene/product mixture occurs because reduced pressure in the reaction line just before the pumping head may cause gas bubbles within the pumping head, leading to pump failures. Just after reaching reflux temperature in the reaction flask, a pump and heater are switched on to feed aqueous sorbitol to the reaction flask. The temperature of the aqueous sorbitol feed is about 95° C. After a period of 15–30 minutes, isosorbide precipitation is observed in the precipitation flask.

At the beginning of the reaction, a minor amount of low-density brown flakes, which are degradation products located at the surface of the xylene layer, are formed which agglomerate after 60–90 minutes. Compared to the flakes, the agglomerates have higher density and combine with the aqueous layer. It is therefore advantageous to pump out the xylene/product solution in a region apart from the surfaces of the xylene layer where the flow velocity is low in order to avoid collection of the agglomerates.

EXAMPLE 2

Figure 3:
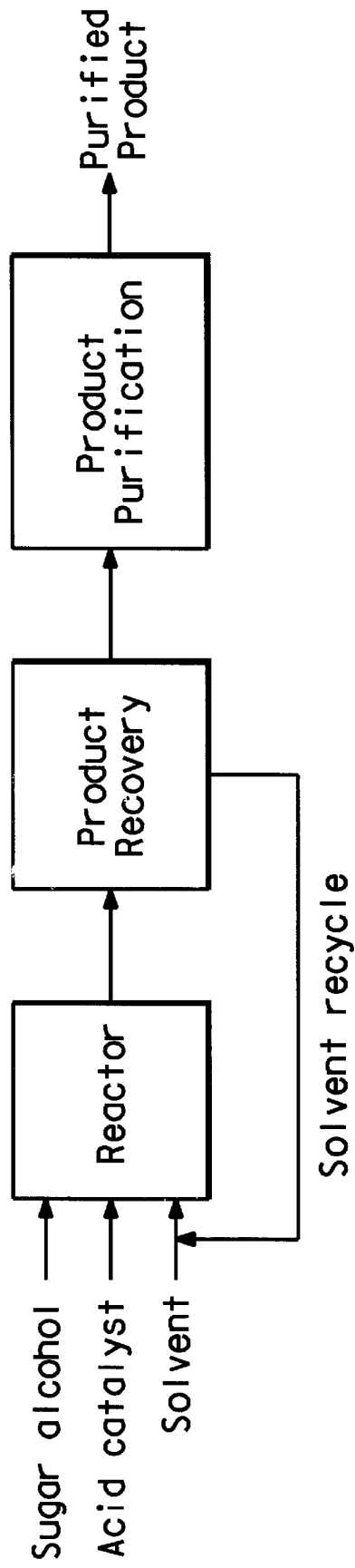
FIG. 3 illustrates a preferred embodiment of the invention wherein the continuous process for the production of anhydrosugar alcohol includes purification.

The process as described in Example 1 is repeated, except that the reaction product dissolved in xylene is added to a solution of methanol and then further purified, as demonstrated generally in FIG. 3.

FIG. 3 depicts a process diagram of the reaction, wherein the sugar alcohol, acid catalyst and solvent are fed into a reactor. As the reaction product is generated, it is recovered in the product recovery area. Here, the crude reaction product is separated from the solvent, which is recycled for use in the reactor. The crude reaction product is then further purified in the stage of product purification, resulting in a highly purified anhydrosugar alcohol.

In this particular reaction, the xylene solvent and methanol form a two-part solution at room temperature in the product recovery stage, wherein the reaction product is extracted into the methanol layer. The methanol layer containing the reaction product is then separated from the xylene by decanting. The methanol containing the reaction product is distilled, and the distillation product is recrystallized. The resulting isosorbide has a purity of >99.8%.

In the examples given in the tables below, dehydrations using various solvents and reaction conditions are described. The starting material (educt) solution employed is an aqueous sugar alcohol solution of the kind produced as a product in the hydrogenation of glucose. In all cases, the sorbitol used is a commercial product of Aldrich having about 97% purity.

EXAMPLE 3

This example demonstrates the use of various solvents in the dehydration reaction.

A reaction as described in Example 1 is performed with 1 ml $H_2SO_4$ conc. catalyst; 2100 ml solvent; a xylene recirculation rate of 3000 ml/h; a sorbitol dosage (in a 45% solution in $H_2O$) of 24 g/h (=132 mMol/h); a reaction flask temperature of 130° to 140° C.; and a precipitation flask temperature of <0° C. The duration of the reaction is approximately 4 hours. Amounts of sorbitol, isosorbide, and intermediates are shown in Table 1.

TABLE 1

|  | Anisole | Dichlorobenzene | Nonane | Xylene |
| --- | --- | --- | --- | --- |
| Educt (mMol): sorbitol | 540 | 530 | 510 | 505 |
| Products (mMol): Sorbitol | 0 | 0 | 0 | 0 |
| Sorbitan | 37 | 9 | 5 | 23 |
| Isosorbide | 349 | 278 | 300 | 400 |
| Yield of isosorbide (in %) | 64 | 52 | 59 | 79 |

As shown in the table, best results are achieved by the use of xylene or anisole as the solvent.

EXAMPLE 4

This example demonstrates the use of various catalysts in the dehydration reaction.

A reaction as described in Example 1 is performed with 2100 ml xylene; a xylene recirculation rate of 2000 ml/h; a sorbitol dosage (in a 45% solution in $H_2O$) of 24 g/h (=132 mMol/h); a reaction flask temperature of 130° to 140° C.; and a precipitation flask temperature of <0° C. The duration of the reaction is approximately 4 hours. Amounts of sorbitol, isosorbide, and intermediates are shown in Table 2.

TABLE 2

|  | $H_2SO_4$ 1 ml | $H_3PO_4$ 20 ml | p-Toluene sulfonic acid 5 g | Methane sulfonic acid 5 ml | BioRad* 50W-X12 16 g | Zeolite** 10 g |
| --- | --- | --- | --- | --- | --- | --- |
| Educt (mMol): sorbitol | 530 | 500 | 565 | 560 | 570 | 555 |
| Products (mMol): Sorbitol | 0 | 32 | 0 | 0 | 0 | 175 |
| Sorbitan | 52 | 225 | 145 | 52 | 41 | 154 |
| Isosorbide | 393 | 137 | 202 | 315 | 360 | 105 |
| Yield of isosorbide (in %) | 74 | 27 | 36 | 56 | 63 | 19 |

*Ion exchanger (sulfonated polystyrene) AG50W-X12 (100–200 mech H form).
**Type H-beta made by Degussa, module 27.

As shown in the table, best results are achieved using $H_2SO_4$ or BioRad 50W-X12 as the catalyst.

EXAMPLE 5

This example demonstrates the effect of different dosages of the starting material sugar alcohol.

A reaction as described in Example 1 is performed with 1 ml $H_2SO_4$ conc. catalyst; 2100 ml xylene; a xylene recirculation rate of 3000 ml/h; a reaction flask temperature of 130° to 140° C.; and a precipitation flask temperature of <0° C. The duration of the reaction is approximately 4 hours. Amounts of sorbitol, isosorbide and intermediates are shown in Table 3.

TABLE 3

| Sorbitol dosage (45% in H$_2$O) | 98 mMol/h | 132 mMol/h | 198 mMol/h | 264 mMol/h |
|---|---|---|---|---|
| Educt (mMol): sorbitol | 336 | 505 | 758 | 1010 |
| Products (mMol): | | | | |
| Sorbitol | 0 | 0 | 0 | 0 |
| Sorbitan | 15 | 23 | 28.5 | 105 |
| Isosorbide | 247 | 400 | 476 | 567 |
| Yield of isosorbide (in %) | 74 | 79 | 63 | 56 |

As shown in the table, yields strongly depend on the feed rates of the starting material

EXAMPLE 6

This example demonstrates the effect of varying the recirculation rate of the solvent.

A reaction as described above is performed with 1 ml H$_2$SO$_4$ conc. catalyst; 2100 ml xylene; a sorbitol dosage (in a 45% solution in H$_2$O) of 24 g/h (=132 mMol/h); a reaction flask temperature of 130° to 140° C.; and a precipitation flask temperature of <0° C. The duration of the reaction is approximately 4 hours. Amounts of sorbitol, isosorbide and intermediates are shown in Table 4.

TABLE 4

| Recirculation rate | 1800 ml/h | 2000 ml/h | 2200 ml/h | 3000 ml/h |
|---|---|---|---|---|
| Educt (mMol): sorbitol*** | 505 | 505 | 505 | 505 |
| Products (mMol): | | | | |
| Sorbitol | 0 | 0 | 0 | 0 |
| Sorbitan | 24 | 33 | 50 | 23 |
| Isosorbide | 320 | 335 | 342 | 400 |
| Yield of isosorbital (in %) | 63 | 66 | 68 | 79 |

As shown in the table, higher recirculation rates of the organic solvent lead to higher yields of product.

EXAMPLE 7

A reaction as described in Example 1 is performed with 1400 ml of xylene; a xylene recirculation rate of 600 ml/h; a sorbitol dosage (in a 45% solution in H$_2$O, additionally containing 0.5% H$_2$SO$_4$) of 24 g/h (=132 mMol/h); a reaction flask temperature of 130° to 140° C.; and a precipitation flask temperature of <0° C. The duration of the reaction is approximately 4 hours, over which time the catalyst is added in a continuous dosage.

Starting Material (sorbitol): 525 mMol

Products: Sorbitol: 0 mMol; sorbitan: 37 mMol; isosorbide: 301 mMol; yield (isosorbide), 57%.

EXAMPLE 8

Separation of the reaction product from the organic solvent may be done by liquid/liquid extraction. For example, at 80° C., 200 ml of a 1.1% solution of isosorbide in xylene is extracted with 20 ml of water. The isosorbide is extracted almost entirely into the aqueous phase, and the xylene layer retains only about 0.04% isosorbide.

EXAMPLE 9

The phase behavior of a three-component system of mixed xylenes, methanol and isosorbide was studied. For each experiment, a three component mixture of isosorbide, methanol and mixed xylenes (20 g total) was prepared by one of two methods.

a) Isosorbide was placed in a small vial and the vial immersed in a preheated (~80° C.) oil bath until the isosorbide melted. To the molten isosorbide was added first methanol and then xylene.

b) Isosorbide and xylene were placed together in a small vial and heated in a preheated (~130° C.) oil bath until the isosorbide dissolved completely. The vial was removed from the oil and allowed to cool to about 50° C. at which time methanol was added.

The vial was sealed, the solution well mixed and allowed to cool to room temperature. After standing undisturbed for at least 15 minutes, the solutions were examined for evidence of phase separation. Table 5 below contains composition information for samples that remained as one phase on standing. Table 6 contains composition information for samples that separated into two phases on standing.

The above examples demonstrate the subject matter of the invention, but are not to be considered limiting and do not define the scope of the invention. The invention is intended to include equivalent methods and materials as known to one in the art, and is further defined by the following claims.

TABLE 5

Single Phase System

| Component weight percent | | |
|---|---|---|
| Isosorbide | Methanol | Xylenes |
| 4.2 | 19.1 | 76.5 |
| 3.5 | 32.0 | 64.4 |
| 2.7 | 49.4 | 48.6 |
| 1.8 | 65.3 | 32.8 |
| 1.1 | 79.1 | 19.8 |
| 23.1 | 38.5 | 38.5 |
| 16.7 | 27.8 | 55.6 |
| 28.6 | 47.6 | 23.8 |
| 32.4 | 54.1 | 13.5 |
| 34.4 | 57.4 | 8.2 |
| 35.3 | 58.8 | 5.9 |
| 36.0 | 60.0 | 4.0 |
| 36.4 | 60.6 | 3.0 |
| 4.1 | 3.1 | 92.9 |
| 4.8 | 6.0 | 89.2 |
| 0.0 | 66.6 | 33.4 |
| 10.0 | 22.0 | 68.0 |
| 20.0 | 28.0 | 52.0 |
| 30.0 | 34.0 | 36.0 |
| 30.0 | 36.0 | 34.0 |
| 40.0 | 34.0 | 26.0 |
| 40.0 | 36.0 | 24.0 |

TABLE 6

Two Phase System

| Component weight percent | | |
|---|---|---|
| Isosorbide | Methanol | Xylenes |
| 4.9 | 5.9 | 89.0 |
| 4.8 | 8.6 | 86.5 |
| 4.6 | 11.9 | 83.4 |
| 10.7 | 17.9 | 71.4 |
| 20.0 | 10.0 | 70.0 |
| 30.0 | 10.0 | 60.0 |
| 30.0 | 20.0 | 50.0 |
| 40.0 | 20.0 | 40.0 |
| 50.0 | 20.0 | 30.0 |

TABLE 6-continued

Two Phase System

Component weight percent

| Isosorbide | Methanol | Xylenes |
|---|---|---|
| 60.0 | 15.0 | 25.0 |
| 30.0 | 30.0 | 40.0 |
| 40.0 | 30.0 | 30.0 |
| 5.0 | 3.0 | 92.0 |
| 20.0 | 7.5 | 72.5 |
| 40.0 | 12.5 | 47.5 |
| 40.0 | 15.0 | 45.0 |
| 50.0 | 15.0 | 35.0 |
| 60.0 | 17.5 | 22.5 |
| 60.0 | 20.0 | 20.0 |
| 70.0 | 15.0 | 15.0 |
| 70.0 | 20.0 | 10.0 |
| 22.2 | 8.3 | 69.4 |
| 25.0 | 15.6 | 59.4 |
| 33.3 | 16.7 | 50.0 |
| 37.5 | 15.6 | 46.9 |
| 50.0 | 21.9 | 28.1 |
| 50.0 | 25.0 | 25.0 |
| 20.0 | 24.0 | 56.0 |
| 20.0 | 26.0 | 54.0 |
| 30.0 | 32.0 | 38.0 |
| 40.0 | 32.0 | 28.0 |
| 11.1 | 8.3 | 80.5 |
| 12.5 | 6.2 | 81.2 |
| 37.5 | 18.8 | 43.7 |
| 57.1 | 21.5 | 21.4 |
| 20.0 | 10.0 | 70.0 |
| 30.0 | 10.0 | 60.0 |
| 30.0 | 20.0 | 50.0 |
| 40.0 | 20.0 | 40.0 |
| 50.0 | 20.0 | 30.0 |
| 60.0 | 15.0 | 25.0 |
| 30.0 | 30.0 | 40.0 |
| 40.0 | 30.0 | 30.0 |
| 12.0 | 12.0 | 76.0 |

What is claimed is:

1. A process for production of anhydrosugar alcohol comprising:

introducing at least one sugar alcohol or monoanhydrosugar alcohol into a reaction vessel;

dehydrating the at least one sugar alcohol or monoanhydrosugar alcohol in the presence of an acid catalyst and a solvent to form a reaction product, which is at least partly soluble in the solvent;

removing water from the reaction vessel;

removing solvent comprising the dissolved reaction product from the reaction vessel;

separating the reaction product from the removed solvent; and recycling the solvent into the reaction vessel, wherein the steps of introducing, removing water, removing solvent and recycling solvent occur simultaneously.

2. The process of claim 1, further including the step of purifying the reaction product.

3. A polymer made by polycondensation of the anhydrosugar alcohol of claim 2 with a multi-carboxylate containing material or carbonic acid containing material wherein the polymer is a polyester, polycarbonate-ester or polycarbonate.

4. A product made with the polymer of claim 3.

5. The product of claim 4, selected from the group consisting of film, fiber, sheet, container and optical disk.

6. The process of claim 1 wherein the reaction product is separated from the removed organic solvent by recrystallization, evaporation or extraction.

7. The process of claim 6 wherein the reaction product is separated from the removed organic solvent by extraction using a lower aliphatic alcohol or water.

8. The process of claim 7 wherein the lower aliphatic alcohol is methanol or ethanol.

9. The process of claim 7 further comprising distilling the separated reaction product.

10. The process of claim 6 comprising recrystallizing the separated reaction product.

11. The process of claim 10 wherein the recrystallization is carried out by melt crystallization.

12. The process of claim 2 wherein the reaction product is purified by distillation.

13. The process of claim 2 wherein the reaction product is purified by recrystallization.

14. The process of claim 13 wherein the recrystallization is melt recrystallization.

15. The process of claim 13 wherein the recrystallization is from methanol or ethanol.

16. The process of claim 13 wherein the reaction product is purified by distillation and recrystallization, forming a purified anhydrosugar alcohol of >99.0% purity.

17. The process of claim 16 wherein the recrystallization is from methanol or ethanol.

18. The process of claim 16 wherein the recrystallization is melt recrystallization.

19. The process of claim 16 wherein the purity is >99.8%.

20. The process of claim 1 wherein the organic solvent forms an azeotropic mixture with water.

21. The process of claim 1 wherein the organic solvent has a boiling point greater than 100° C.

22. The process of claim 1 wherein the organic solvent is selected from the group consisting of xylene, anisole and nonane.

23. The process of claim 22 wherein the organic solvent is xylene.

24. The process of claim 1 wherein the sugar alcohol is a penite, hexite or a mixture thereof.

25. The process of claim 1 wherein the sugar alcohol is sorbitol.

26. The process of claim 1 wherein the acid catalyst is selected from the group consisting of a soluble acid, an acid anion exchange resin or an inorganic ion exchange resin.

27. The process of claim 26 wherein the soluble acid is selected from the group consisting of sulfuric acid, phosphoric acid, p-toluene sulfonic acid and methanesulfonic acid.

28. The process of claim 27 wherein the soluble acid is sulfuric acid.

* * * * *